United States Patent [19]

Wamprecht et al.

[11] Patent Number: 5,552,507
[45] Date of Patent: Sep. 3, 1996

[54] DIISOCYANATES AND PROCESSES FOR THEIR PRODUCTION AND USE

[75] Inventors: Christian Wamprecht, Neuss; Klaus Jost, Dormagen; Stefan Penninger, Pulheim, all of Germany

[73] Assignee: Bayer Aktiengesellschaft, Leverkusen, Germany

[21] Appl. No.: 434,254

[22] Filed: May 3, 1995

[30] Foreign Application Priority Data

May 17, 1994 [DE] Germany .................. 44 17 186.2

[51] Int. Cl.$^6$ ............ C08G 18/77; C07D 251/34; C07C 69/34; C07C 265/02
[52] U.S. Cl. .............. 528/44; 528/59; 528/73; 528/76; 528/80; 528/85; 540/202; 544/193; 544/222; 560/129; 560/130; 560/145; 560/179; 560/330; 560/335; 560/338; 560/346; 560/347; 560/355
[58] Field of Search .................. 560/129, 130, 560/145, 179, 330, 335, 338, 346, 347, 355; 540/202; 544/193, 222; 528/44, 59, 76, 80, 85, 73

[56] References Cited

U.S. PATENT DOCUMENTS

| | | | |
|---|---|---|---|
| 3,367,920 | 2/1968 | Wasserman et al. | 528/44 |
| 3,567,763 | 3/1971 | Emmons et al. | 560/129 |
| 3,912,770 | 10/1975 | Botta et al. | 560/129 |
| 4,224,238 | 9/1980 | Nagato et al. | 560/339 |
| 4,574,059 | 3/1986 | Kervennal et al. | 560/347 |
| 4,879,408 | 11/1989 | Knöfel et al. | 560/330 |

FOREIGN PATENT DOCUMENTS 965474  7/1964  United Kingdom .

*Primary Examiner*—James J. Seidleck
*Assistant Examiner*—Rabon Sergent
*Attorney, Agent, or Firm*—Joseph C. Gil; Lyndanne M. Whalen

[57] ABSTRACT

Diisocyanates containing carboxylic acid ester groups corresponding to the formula:

$$OCN-CH_2-CH(R)-CH_2-C(OR^1)(CO-OR^1)-CH_2-CH(R)-CH_2-NCO \quad (I)$$

in which R and $R^1$ represent specified groups are produced by phosgenation of the corresponding diamines, optionally present in the form of an ammonium salt. These diisocyanates are useful as starting materials in the production of plastics containing urethane and/or urea groups and as starting materials for the production of intermediate products used for the production of such plastics.

4 Claims, No Drawings

DIISOCYANATES AND PROCESSES FOR THEIR PRODUCTION AND USE

BACKGROUND OF THE INVENTION

The present invention relates to novel diisocyanates corresponding to a specified formula, to a process for the production of these diisocyanates and to a process for the production of plastics containing urethane and/or urea groups from these novel diisocyanates.

SUMMARY OF THE INVENTION

It is an object of the present invention to provide novel diisocyanates.

It is also an object of the present invention to provide diisocyanates which contain aliphatically bound isocyanate groups and are suitable for the production of light-stable plastics.

It is another object of the present invention to provide diisocyanates which are low viscosity, high boiling liquids or solids with low melting points.

It is a further object of the present invention to provide diisocyanates which contain carboxylic acid ester groups.

It is also an object of the present invention to provide a process for the production of novel diisocyanates which contain carboxylic acid ester groups.

It is an additional object of the present invention to provide a process for the production of light-stable, weather resistant plastics.

These and other objects which will be apparent to those skilled in the art are accomplished by the diisocyanates represented by the formula specified herein. These diisocyanates are made by phosgenating the diamine corresponding to the desired diisocyanate. Plastics may be made from these diisocyanates by the isocyanate polyaddition process.

DETAILED DESCRIPTION OF THE INVENTION

This invention relates to new diisocyanates corresponding to the following formula:

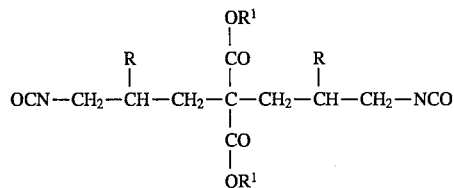

(I)

in which

R represent the same or different radicals and stand for hydrogen or an aliphatic hydrocarbon radical containing from 1 to 4 carbon atoms and $R^1$ represent the same or different radicals and stand for an aliphatic, araliphatic and/or cycloaliphatic radical containing from 1 to 12 carbon atoms.

The present invention also relates to a process for the production of these diisocyanates in which diamines corresponding to the following formula:

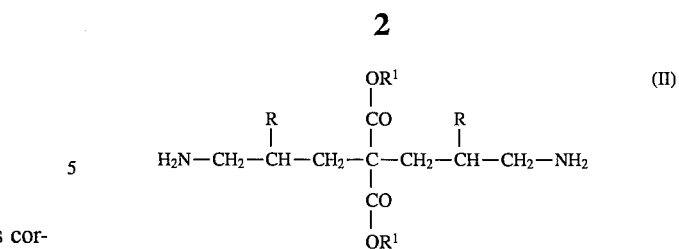

(II)

optionally present in the form of an ammonium salt, are phosgenated by any of the known methods.

The new diisocyanates of the present invention contain carboxylic acid ester groups. These diisocyanates are characterized by a number of valuable properties. One of these properties is the presence of aliphatically bound isocyanate groups which make them particularly suitable for the production of light-stable, weather-resistant plastics containing urethane and/or urea groups or for intermediate products used in the production of such plastics.

Another advantageous property of these new diisocyanates is the fact that they are low-viscosity high-boiling liquids or solids with low melting points. These properties make them superior in physiological terms to known aliphatic diisocyanates (e.g., hexamethylene diisocyanate) which have far higher vapor pressures.

An additional beneficial property of the diisocyanates of the present invention is the presence of carboxylic acid ester groups. These carboxylic acid ester groups make it possible to vary the properties of the diisocyanate such as viscosity, solubility in organic solvents and/or compatibility with reactants within wide limits by variation of the inert substituents R and, more particularly, $R^1$.

The diisocyanates of the present invention are produced by phosgenating the diamines on which they are based. These diamines are represented by Formula II. These diamines may optionally be used in the form of an ammonium salt or a dihydrochloride (which form is particularly preferred) by any of the known methods. In Formula II and in each of the formulae which follow, the substituents R and $R^1$ are as defined above for Formula I. R preferably represents hydrogen or a methyl group and $R^1$ preferably represents a methyl or ethyl group.

The diamines to be used in the process for producing the diisocyanates of the present invention may be produced, for example, by the following two-stage reaction. In a first stage, 2 moles of a nitrile corresponding to the formula:

(III)

are reacted with 1 mole of a malonic acid ester corresponding to the formula:

(IV)

to form a dinitrile corresponding to the formula:

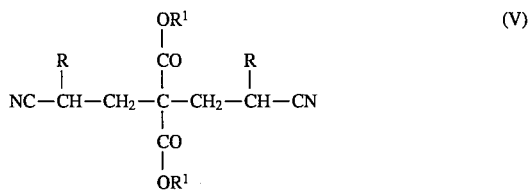

(V)

This reaction is described, for example, in "Organikum", 15th Edition, VEB Deutscher Verlag der Wissenschaften, Berlin 1977, pages 633 et seq. This known reaction may be carried out at 0° to 80° C. (preferably at 30° to 45° C.) in the presence of from 1 to 5 mole-%, based on the quantity of malonic acid ester used, of a strong base such as sodium or potassium hydroxide. An alcoholic solvent may optionally be present. A small quantity of a suitable alcohol, which preferably corresponds to the residue of the malonic acid ester used, is often used as solvent for the base.

Nitriles which are suitable for use in this first stage include: acrylonitrile, methacrylonitrile, 2-ethyl acrylonitrile, 2-propyl acrylonitrile and 2-butyl acrylonitrile. Acrylonitrile and methacrylonitrile are preferred. Acrylonitrile is particularly preferred.

Suitable malonic acid esters include: malonic acid dimethyl ester, malonic acid diethyl ester, malonic acid di-n-propyl ester, malonic acid diisopropyl ester, malonic acid di-n-butyl ester, malonic acid diisobutyl ester, malonic acid di-tert.butyl ester, malonic acid di-n-hexyl ester, malonic acid di-2-ethylhexyl ester, malonic acid dibenzyl ester and malonic acid dicyclohexyl ester. Malonic acid dimethyl ester and malonic acid diethyl ester are preferred.

The dinitriles corresponding to Formula V are converted into the diamines corresponding to Formula II in the second stage of the procedure for their production. This conversion may be accomplished, for example, by catalytic hydrogenation in the presence of a weakly polar or apolar organic solvent and ammonia at 80° to 130° C. under a pressure of 120 to 200 bar in the presence of a catalyst such as Raney cobalt or Raney nickel. Conversion of the dinitrile to the corresponding diamine may also be accomplished by hydrogenating the dinitrile in the presence of a carboxylic acid solvent and hydrogen chloride or any other acid capable of forming ammonium salts with the diamine at a temperature of from 10° to 100° C. under a pressure of 20 to 150 bar. Catalysts useful in this hydrogenation process include those based on platinum or palladium, such as platinum metal, palladium metal and any of the oxides of these metals. When the hydrogenation reaction is carried out in an acidic medium, the diamine accumulates as the corresponding ammonium salt. The hydrogenation reaction is preferably carried out in an acidic medium.

Prior to hydrogenation, the dinitrile corresponding to Formula II is preferably dissolved to form a solution in which from 5 to 40% by weight of the solution is the dinitrile. Solvents which are useful for making such solutions when the hydrogenation is carried out in an alkaline medium such as ammonia include: methanol, ethanol, isopropanol, dioxane, tetrahydrofuran and mixtures thereof. If the hydrogenation reaction is carried out in an acidic medium, suitable solvents for making the dinitrile solution include: formic acid, acetic acid, propionic acid, chloroacetic acid and mixtures thereof.

If the hydrogenation is carried out in the presence of a strong acid capable of forming an ammonium salt, the diamine is obtained directly in the form of an ammonium salt. In this case, the hydrogen chloride (mentioned by way of example as being useful in the hydrogenation reaction) may be replaced by another acid such as hydrogen bromide, sulfuric acid or phosphoric acid. Hydrogen chloride is, however, the preferred acid.

The solution of the diamine corresponding to Formula II which is obtained by the hydrogenation reaction may be freed from catalyst by filtration. The solvent may be removed by distillation. After removal of the catalyst and, optionally the solvent, the diamine corresponding to Formula V may be delivered without further working up to the phosgenation process in solution form in a solvent which is suitable for the phosgenation reaction. However, the diamine, more particularly corresponding diamine hydrochloride, may also be isolated in pure form and subsequently delivered to the phosgenation reaction.

To carry out the phosgenation process of the present invention, the diamine corresponding to Formula II or a corresponding diamine hydrochloride is phosgenated in known manner. One suitable phosgenation method is the cold-hot phosgenation process (W. Siefken, Annalen der Chemie, 562., (1949), pages 75 et seq.). The product diisocyanate corresponding to Formula 1 is then worked up by distillation. The phosgenation reaction is preferably carried out in the presence of a suitable solvent such as chlorobenzene or o-dichlorobenzene.

The diisocyanates represented by Formula I are a new type of aliphatic diisocyanate characterized, in particular, by the carboxylic acid ester group substituents.

The diisocyanates of the present invention are valuable starting materials for the production of plastics containing urethane and/or urea groups by the isocyanate polyaddition process. These diisocyanates may be reacted in known manner with the usual isocyanate-reactive compounds, particularly those compounds containing isocyanate-reactive hydroxyl and/or amino groups. The diisocyanates represented by Formula I may be used either instead of or in combination with known polyisocyanates.

The diisocyanates of the present invention are also suitable for the production of intermediate products to be used for the production of such plastics. Preferred intermediate products formed from the diisocyanates of the present invention are modified polyisocyanates which, in turn, are used as starting materials for the production of plastics containing urethane and/or urea groups. Modified polyisocyanates may contain allophanate, biuret, isocyanurate, urethane and/or uretdione groups. Until now, such modified polyisocyanates have generally been produced from polyisocyanates such as hexamethylene diisocyanate and/or isophorone diisocyanate. In the production of modified polyisocyanates from the diisocyanates of the present invention, the diisocyanate corresponding to Formula I is used in any of the known modification processes either instead of or in admixture with any of the known diisocyanates known to be useful for producing modified polyisocyanates.

The diisocyanates of the present invention and their modification products containing isocyanate groups are particularly suitable as the polyisocyanate component used to produce polyurethane adhesives and coating compositions.

Having thus described our invention, the following Examples are given as being illustrative thereof. All percentages given in the Examples are percentages by weight. The "HC value" indicates the content of hydrolysable chlorine.

EXAMPLES

Example 1 a) Di-(2-cyanoethyl)-malonic acid diethyl ester 1399 g of acrylonitrile (26.4 moles) were added with stirring at room temperature to a mixture of 1920 g of malonic acid diethyl ester (12 moles), 12 g of potassium hydroxide and 120 g of ethanol at a rate such that the temperature could be kept at 35° to 40° C., optionally by cooling. After the addition, the mixture was left standing overnight without stirring. The crystal sludge which formed was stirred with water, filtered under suction and recrystallized from ethanol. Colorless crystals melting at 61.7° C. were obtained in a yield of 2947 g (92.3% of theoretical).

b) Di-(3-aminopropyl)-malonic acid diethyl ester dihydrochloride 100 g of di-(2-cyanoethyl)-malonic acid diethyl ester (obtained in 1.a)), 800 ml of glacial acetic acid and 10 g of platinum oxide were introduced into a 1.3 liter stirred autoclave which was made of a corrosion-resistant metal alloy. After purging three times with nitrogen, 28 g of hydrogen chloride were added, hydrogen was introduced to a pressure of 40 bar and the contents of the autoclave were hydrogenated at 20° to 40° C. until a constant pressure had been established. The contents of the autoclave were then stirred for 1 hour at 35° C. under a hydrogen pressure of 100 bar. The autoclave was then vented, emptied and rinsed with glacial acetic acid.

The product solutions of 10 autoclave batches were filtered through a suction filter and the solvent of the filtrate was distilled off in a rotary evaporator at a maximum temperature of 100° C. The resulting tough and resilient product containing glacial acetic acid was stirred with chlorobenzene. Crystallization occurred. The crystal sludge was filtered off under suction, briefly washed with acetone and suction-dried. After drying for 20 hours in a vacuum drying cabinet at around 90 to 100° C/15 mbar, the product accumulated in the form of an almost colorless powder melting at 190° C. Yield: 1210 g (94% of the theoretical).

IR, $^1$H-NMR and $^{13}$C-NMR spectra confirmed the structure of the product.

c) Di-(3-isocyanatopropyl)-malonic acid diethyl ester c1) Phosgenation and solvent removal Gaseous phosgene was introduced under reflux into a suspension of 62.3 g of di-(3-aminopropyl)-malonic acid diethyl ester dihydrochloride (from 1.b)) in 1.5 liters of chlorobenzene until the suspension became clear. The suspension was then dephosgenated with nitrogen and the solvent was subsequently distilled off in vacuo, leaving 58.2 g of di-( 3-isocyanatopropyl)-malonic acid diethyl ester as crude product. NCO content: 24.2% (theoretical: 25.8%).

c2) Heating and distillation

In a 500 ml spherical flask with a Claisen bridge, 420 g of di-( 3-isocyanatopropyl)-malonic acid diethyl ester (crude product of 1.c)) were heated for 25 minutes at around 180° C./approx. 0.3 mbar and subsequently subjected to flash distillation (25 g bottom product). The HC value was 950 ppm.

For fine distillation, 355 g of diisocyanate were introduced into a two-necked flask equipped with a Vigreux column, a Liebig condenser and an exchangeable vacuum receiver. At a distillation rate of approx. 1 drop/second, 5 g of first runnings were removed and the product distilled over at a head temperature of 164° C. under a pressure of 0.1 mbar (6 g bottom product). The yield of colorless liquid was 342 g (96% of the theoretical). NCO content: 24.9% (theoretical: 25.8%), HC value 232 ppm.

IR, $^1$H-NMR, $^{13}$C-NMR, and mass spectra as well as chemical analysis confirmed the structure of the product as that recited above.

| $C_{15}H_{22}N_2O_6$ (326) | calculated: | C: 55.2% | H: 6.75% | N: 8.59% |
| --- | --- | --- | --- | --- |
| | found: | C: 55.4% | H: 6.99% | N: 8.76% |

Example 2 a) Di-(2-cyanoethyl)-malonic acid dimethyl ester 700 g of acrylonitrile (13.2 moles) were added dropwise with stirring at room temperature to a mixture of 792 g of malonic acid dimethyl ester (6 moles), 6 g of potassium hydroxide and 60 g of ethanol at a rate such that the temperature could be kept at 35° to 40° C., optionally by cooling. After the addition, the mixture was left standing overnight without stirring. The crystal sludge formed was stirred with water/ethanol, filtered under suction and dried. Colorless crystals melting at 143° C. were obtained in a yield of 1173 g (82% of the theoretical).

b) Di-(3-aminopropyl)-malonic acid dimethyl ester di-hydrochloride 100 g of di-(2-cyanoethyl)-malonic acid dimethyl ester (obtained in 2.a)) were hydrogenated as in Example 1b). 1240 g of substantially colorless crystals (92.8% of theoretical) melting at 210° C. (decomposition) were obtained after working up of 10 autoclave batches.

$^1$H-NMR and $^3$C-NMR spectra confirmed the structure of the product.

c) Di-(3-isocyanatopropyl)-malonic acid dimethyl ester c1) Phosgenation and solvent removal Gaseous phosgene was introduced under reflux into a suspension of 60.5 g of di-(3-aminopropyl)-malonic acid dimethyl ester dihydrochloride (obtained in 2.b)) in 1.5 liters of o-dichlorobenzene until the suspension became clear. The suspension was then dephosgenated with nitrogen and the solvent was subsequently distilled off in vacuo, leaving 56.6 g of di-(3-isocyanatopropyl)-malonic acid dimethyl ester as crude product. NCO content: 29.6% (theoretical: 28.19%).

c2) Heating and distillation

In a 500 ml spherical flask with a Claisen bridge, 400 g of di-( 3-isocyanatopropyl)-malonic acid dimethyl ester (crude product from 2.cl)) were heated for 40 minutes at around 185° C./approx. 1.5 mbar and subsequently subjected to flash distillation (20 g bottom product). The HC value was 640 ppm.

For fine distillation, 350 g of diisocyanate were introduced into a 500 ml two-necked flask equipped with a Vigreux column, a Liebig condenser and an exchangeable vacuum receiver. At a distillation rate of approx. 1 drop/second, 6 g of first runnings were removed and the product distilled over at a head temperature of 180° C. under a pressure of 0.7 mbar (8 g bottom product). The yield of colorless liquid was 336 g (96% of the theoretical). NCO content: 27.45% (theoretical: 28.19%), HC value 248 ppm.

IR, $^1$H-NMR, $^{13}$C-NMR and mass spectra as well as chemical analysis confirmed that the product had the structure recited above.

| $C_{13}H_{18}N_2O_6$ (298) | calculated: | C: 55.3% | H: 6.04% | N: 9.40% |
| --- | --- | --- | --- | --- |
| | found: | C: 52.4% | H: 5.99% | N: 9.51% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate corresponding to the formula:

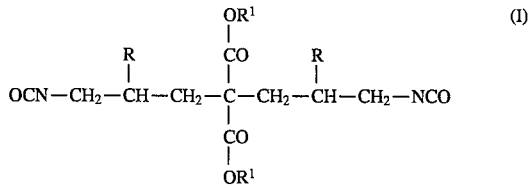

in which

R represent, the same or different radicals and stand for hydrogen or an aliphatic hydrocarbon radical containing from 1 to 4 carbon atoms and $R^1$ represent the same or different radicals and stand for an aliphatic, araliphatic or cycloaliphatic radical containing from 1 to 12 carbon atoms.

2. The diisocyanate of claim 1 in which R represents hydrogen or a methyl group and $R^1$ represents a methyl or ethyl group.

3. A modified isocyanate containing allophanate, biuret, isocyanurate, urethane or uretdione groups which is produced from the diisocyanate of claim 1.

4. A plastic containing urethane and/or urea groups which is a reaction product of the diisocyanate of claim 1 with an isocyanate-reactive compound.

* * * * *